US011590280B2

(12) United States Patent
Wine et al.

(10) Patent No.: US 11,590,280 B2
(45) Date of Patent: Feb. 28, 2023

(54) MODULAR INTRAVENOUS ASSEMBLY

(71) Applicant: CareFusion 303, Inc., San Diego, CA (US)

(72) Inventors: Jason Wine, Placentia, CA (US); George Mansour, Diamond Bar, CA (US)

(73) Assignee: CAREFUSION 303, INC., San Diego, CA (US)

( * ) Notice: Subject to any disclaimer, the term of this patent is extended or adjusted under 35 U.S.C. 154(b) by 368 days.

(21) Appl. No.: 16/886,388

(22) Filed: May 28, 2020

(65) Prior Publication Data

US 2021/0369960 A1   Dec. 2, 2021

(51) Int. Cl.
| | |
|---|---|
| A61M 5/14 | (2006.01) |
| A61M 5/168 | (2006.01) |
| A61M 39/24 | (2006.01) |
| A61M 39/28 | (2006.01) |
| A61M 5/165 | (2006.01) |

(52) U.S. Cl.
CPC ...... *A61M 5/16813* (2013.01); *A61M 5/1411* (2013.01); *A61M 5/165* (2013.01); *A61M 5/16881* (2013.01); *A61M 39/24* (2013.01); *A61M 39/28* (2013.01); *A61M 2005/1657* (2013.01); *A61M 2039/2406* (2013.01); *A61M 2205/7527* (2013.01); *A61M 2205/7536* (2013.01)

(58) Field of Classification Search
CPC ............ A61M 5/16813; A61M 5/1411; A61M 39/28; A61M 5/16881; A61M 5/1413
See application file for complete search history.

(56) References Cited

U.S. PATENT DOCUMENTS

| | | | |
|---|---|---|---|
| 4,269,222 A * | 5/1981 | Palti .................... | A61M 5/1411 137/433 |
| 4,361,147 A * | 11/1982 | Aslanian ................ | G01F 13/00 604/249 |
| 5,195,986 A * | 3/1993 | Kamen ................... | G01F 17/00 604/153 |
| 6,213,986 B1 | 4/2001 | Darling, Jr. | |
| 7,232,420 B1 | 6/2007 | Abulhaj | |
| 2016/0213861 A1* | 7/2016 | Whitaker ............. | A61M 5/1411 |
| 2018/0304009 A1* | 10/2018 | Baid ....................... | A61M 5/36 |

OTHER PUBLICATIONS

International Search Report and Written Opinion for Application No. PCT/US2021/034343, dated Sep. 15, 2021, 18 pages.

* cited by examiner

*Primary Examiner* — Jenna Zhang
(74) *Attorney, Agent, or Firm* — Morgan, Lewis & Bockius, LLP

(57) ABSTRACT

Modular intravenous (IV) assemblies are provided. The modular IV assembly includes a drip chamber having a body and an inlet connector, a base housing coupled directly to a base portion of the drip chamber, the base housing having an inlet port in fluid connection with the drip chamber and a flow path cavity in fluid connection with the inlet port and a flow control assembly coupled directly to a first portion of the base housing. Any of a filter assembly, an anti-run dry member, a check valve and an air vent assembly may be included in the modular IV assembly. IV sets and methods of use are also provided.

20 Claims, 10 Drawing Sheets

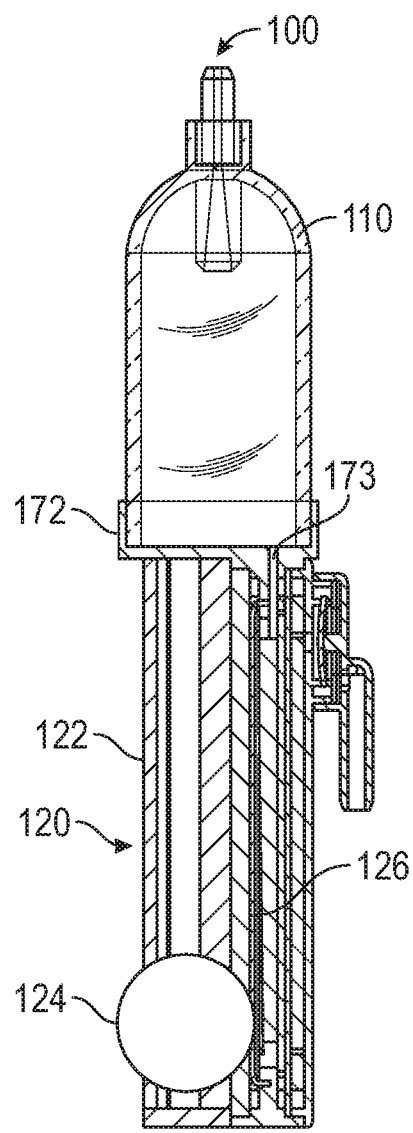
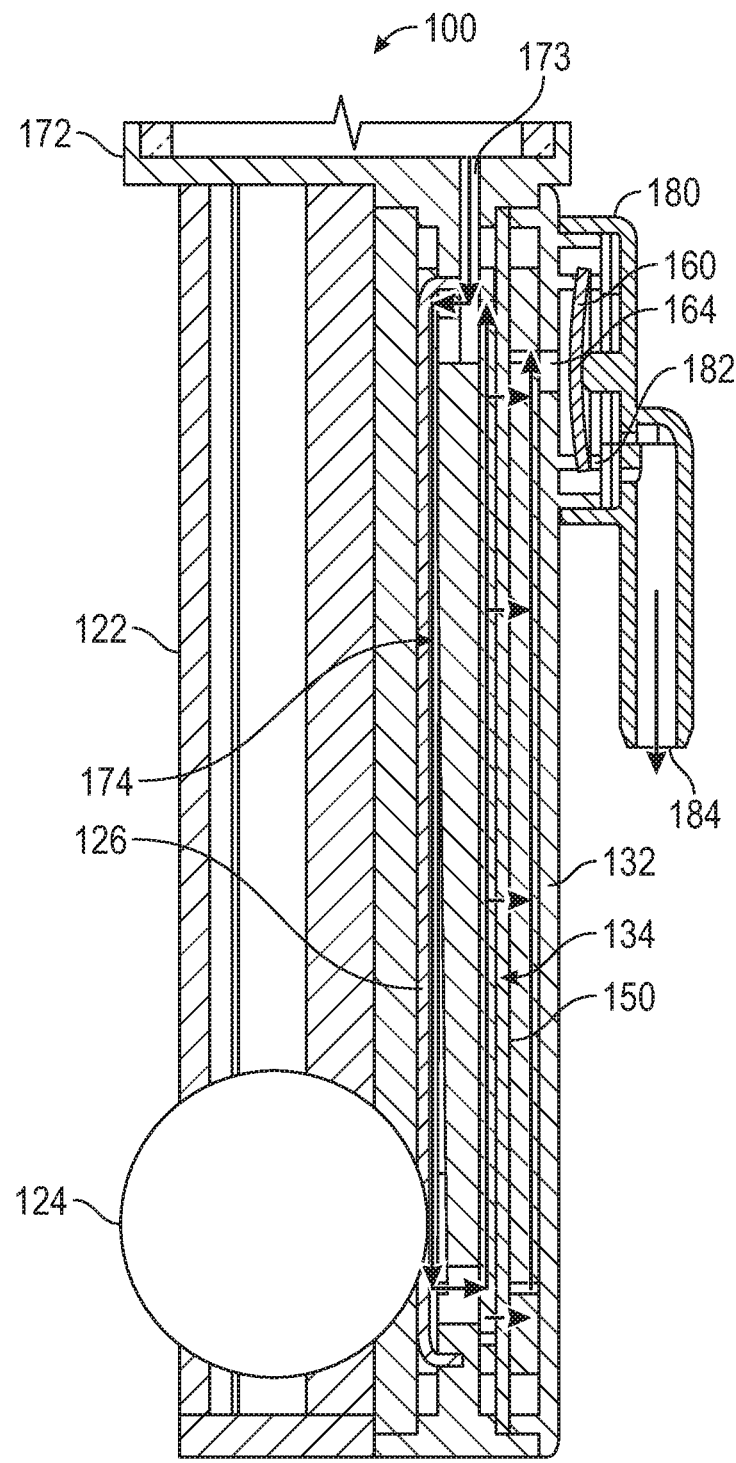
FIG. 6
FIG. 7

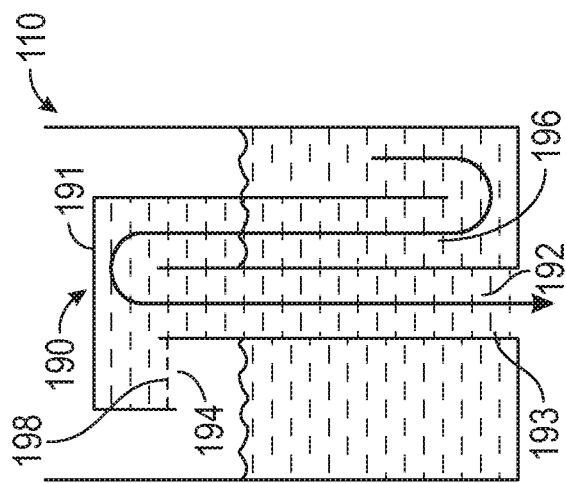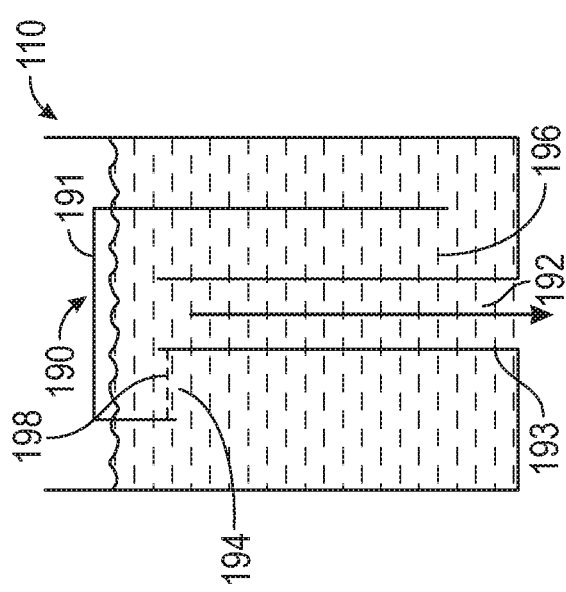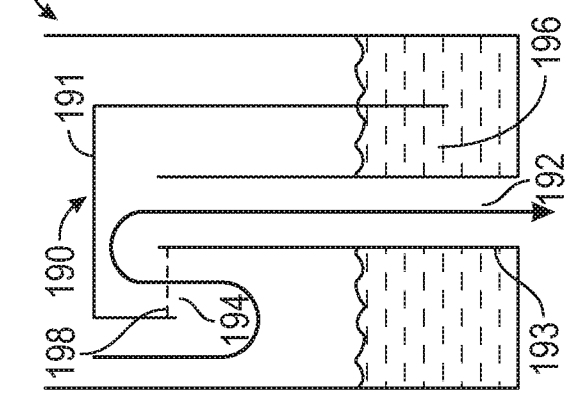

MODULAR INTRAVENOUS ASSEMBLY

CROSS-REFERENCES TO RELATED APPLICATIONS

N/A

BACKGROUND

Intravenous (IV) infusion sets typically include several components each having a core function, such as drip chambers, roller clamps, pinch clamps, filters and check valves. These components are typically coupled to each other by lengths of IV tubing to provide a complete IV infusion set that is packaged as a ready to use disposable IV set. Such an IV infusion set has a significant number of IV tubing connections, which provides a correspondingly increased risk of connection leakage as the number of IV tubing connections grows larger. Each separate component also provides a different interface point to a user. These factors lead to higher manufacturing complexity and costs.

It is desirable to provide a modular IV assembly that combines many IV component core functions into one device, thus reducing manufacturing complexity and costs, as well as improving usability by the user.

SUMMARY

The present disclosure provides modular IV assemblies that combine core functions of several IV infusion set components.

In one or more embodiments, a modular intravenous (IV) assembly is provided. The modular IV assembly includes a drip chamber having a body and an inlet connector. The modular IV assembly also includes a base housing coupled directly to a base portion of the drip chamber, the base housing having an inlet port in fluid connection with the drip chamber and a flow path cavity in fluid connection with the inlet port. The modular IV assembly further includes a flow control assembly coupled directly to a first portion of the base housing. The flow control assembly includes a roller housing, a roller and a flow control membrane disposed between the roller and the flow path cavity in the base housing.

In one or more aspects, the flow path cavity comprises a first flow area having a constant width and a varying depth, and a second flow area having a varying width and a constant depth. In one or more aspects, the flow control assembly is configured to prevent fluid flow through the base housing when the roller is engaged with the flow control membrane adjacent to a start position of the first flow area. In one or more aspects, the flow control assembly is configured to provide full fluid flow through the base housing when the roller is engaged with the flow control membrane adjacent to an end portion of the second flow area. In one or more aspects, the flow control assembly is configured to provide increasing fluid flow through the base housing as the roller engaged with the flow control membrane moves from an end portion of the second flow area.

In one or more aspects, a filter assembly is coupled directly to a second portion of the base housing. In one or more aspects, the first and second portions are on opposing surfaces of the base housing. In one or more aspects, the filter assembly includes a filter housing coupled directly to the second portion of the base housing and a filter membrane disposed between the filter housing and the second portion of the base housing. In one or more aspects, the filter membrane comprises a hydrophilic material that prevents gas from passing through the filter membrane when the filter membrane is wetted. In one or more aspects, a first surface of the filter membrane is disposed adjacently at a distance from an inner surface of the second portion of the base housing, and wherein a space between the inner surface of the second portion and the first surface of the filter membrane is configured to provide a flow path for fluid entering the second portion of the base housing from the flow control assembly. In one or more aspects, a second surface of the filter membrane is disposed adjacently at a distance from an inner surface of the filter housing, and wherein a space between the inner surface of the filter housing and the second surface of the filter membrane is configured to provide a flow path for fluid passing through the filter membrane.

In one or more aspects, an anti-run dry member including one of an individual layer disposed on the filter membrane and an integrally formed material comprising the filter membrane is included. In one or more aspects, a filter housing coupled directly to the second portion of the base housing, a fluid exit housing coupled directly to the filter housing and a one-way check valve disposed between an exit cavity in an outer surface of the filter housing and the fluid exit housing, the check valve configured to allow fluid to flow out from the exit cavity through an exit port in the fluid exit housing while preventing fluid from flowing in the opposing direction into the exit cavity. In one or more aspects, the fluid exit housing, the check valve and the exit cavity are disposed at a top portion of the base housing adjacent to the drip chamber. In one or more aspects, the fluid exit housing, the check valve and the exit cavity are disposed at a bottom portion of the base housing.

In one or more aspects, an air vent assembly is coupled directly to a second portion of the base housing, wherein the first and second portions are on opposing surfaces of the base housing, the air vent assembly including a vent cavity disposed in the second portion of the base housing, a vent port disposed in the vent cavity, the vent port coupled to an air flow path in the base housing and an air vent membrane disposed in the vent cavity. In one or more aspects, the air vent membrane comprises a small pore hydrophobic material that prevents liquid from passing through the air vent membrane into the vent port while allowing gas to pass through the air vent membrane and vent out through the vent port. In one or more aspects, the drip chamber includes a self-leveling assembly having a bottom housing portion disposed at the base portion of the drip chamber and adjacent to the base housing, a leveling outlet port aligned with the inlet port in the base housing, first and second leveling inlet ports disposed adjacent opposing sides of the leveling outlet port and a barrier disposed within the first leveling inlet port.

In one or more embodiments, an intravenous (IV) set is provided. The IV set includes a modular IV assembly having a drip chamber with a body and an inlet connector, a base housing coupled directly to a base portion of the drip chamber, the base housing having an inlet port in fluid connection with the drip chamber and a flow path cavity in fluid connection with the inlet port and a flow control assembly coupled directly to a first portion of the base housing, the flow control assembly including a roller housing, a roller and a flow control membrane disposed between the roller and the flow path cavity in the base housing. The IV set also includes a fluid container coupled to the inlet connector of the drip chamber by a first IV tube. The IV set further includes a fluid delivery member coupled to the modular IV assembly by a second IV tube.

In one or more embodiments, a method of delivering a medical fluid is provided. The method includes coupling a fluid container to a modular intravenous (IV) assembly with a first IV tube, the modular IV assembly including a drip chamber having a body and an inlet connector, a base housing coupled directly to a base portion of the drip chamber, the base housing having an inlet port in fluid connection with the drip chamber and a flow path cavity in fluid connection with the inlet port and a flow control assembly coupled directly to a first portion of the base housing, the flow control assembly including a roller housing, a roller and a flow control membrane disposed between the roller and the flow path cavity in the base housing. The method also includes coupling a fluid delivery member to the modular IV assembly with a second IV tube. The method further includes adjusting a fluid flow rate from the modular IV assembly to the fluid delivery member by moving the roller in the flow control assembly.

Additional features and advantages of the disclosure will be set forth in the description below and, in part, will be apparent from the description or may be learned by practice of the disclosure. The objectives and other advantages of the disclosure will be realized and attained by the structure particularly pointed out in the written description and claims hereof as well as the appended drawings.

It is to be understood that both the foregoing general description and the following detailed description are exemplary and explanatory and are intended to provide further explanation of the disclosure as claimed.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

FIG. 6 is a cross-sectional side view of the modular IV assembly of FIG. 2, according to some aspects of the disclosure.

FIG. 7 is an enlarged partial view of the modular IV assembly of FIG. 6, according to some aspects of the disclosure.

FIGS. 20-22 are schematic views depicting the operation of the self-leveling assembly of FIG. 19.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

IV infusion sets may be formed from any combination of infusion components and tubing. Typically, the infusion components and tubing are disposable products that are used once and then discarded. The infusion components and tubing may be formed from any suitable material (e.g., plastic, silicone, rubber). An issue in manufacturing IV infusion sets is joining multiple tubing and the infusion components to obtain secure leak free joints with desired fluid flow. An issue in using IV infusion sets is that having many separate components provides many interface points to a user.

Figure 1:
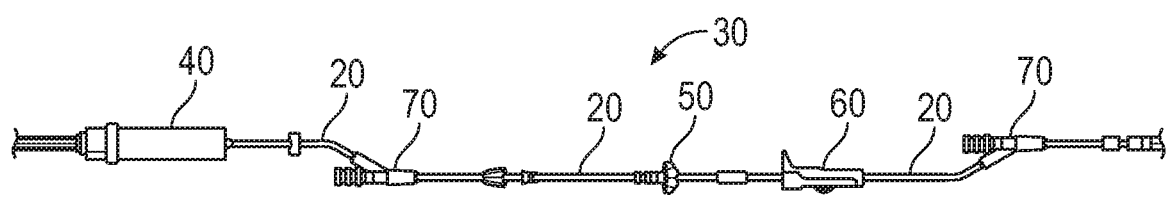
FIG. 1 depicts a schematic view of a typical assembled infusion set.
Figure 4:
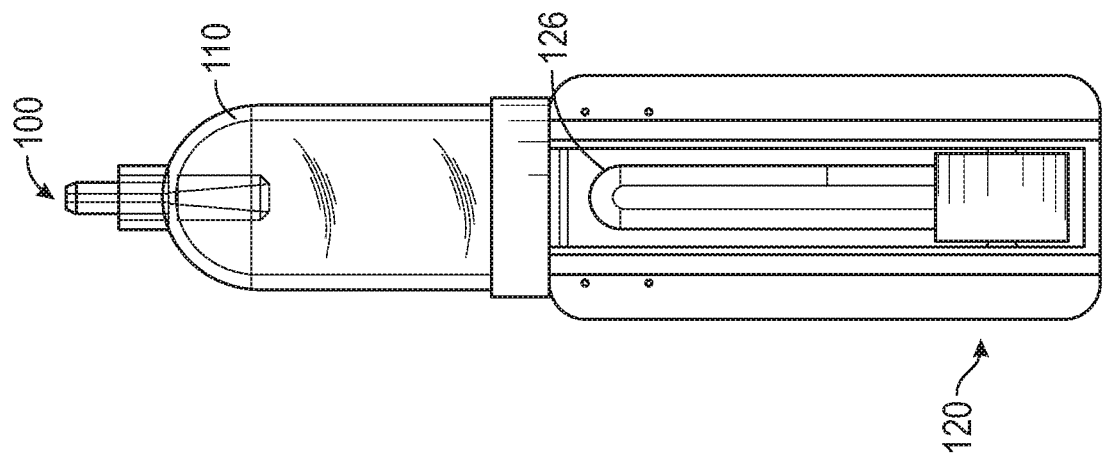
FIG. 4 is a front view of the modular IV assembly of FIG. 2, according to some aspects of the disclosure.
Figure 3:
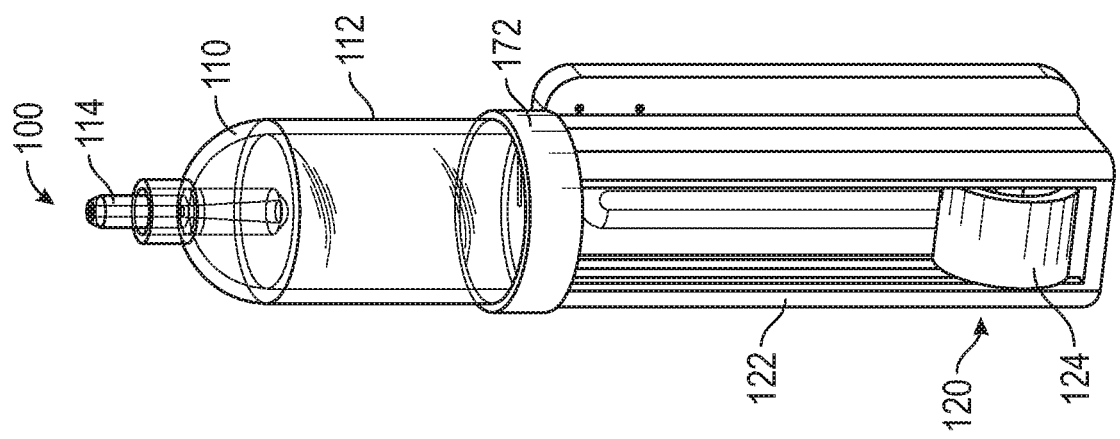
FIG. 3 is another perspective view of the modular IV assembly of FIG. 2, according to some aspects of the disclosure.
Figure 2:
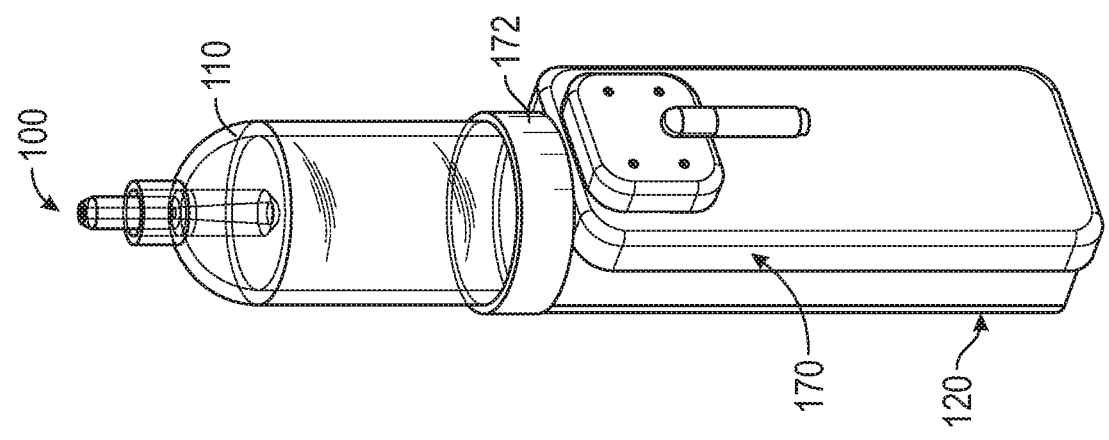
FIG. 2 is a perspective view of a modular IV assembly, according to some aspects of the disclosure.

As shown in FIG. 1, a typical infusion set 30 may include a drip chamber 40, a check valve 50, a roller clamp 60 and Y-junctions 70, all connected together by tubing 20. A typical infusion set 30 can include additional infusion components (e.g., pinch clamps, filters) and can be formed of any combination of components and the tubing 20.

According to some aspects of the disclosure, a modular IV assembly combines IV component core functions into one device, thus reducing the number of tubing connections required for an IV infusion set. According to some aspects of the disclosure, the modular IV assembly provides a design architecture that can be more easily automated than a convention IV infusion set.

According to some aspects of the disclosure, the modular IV assembly provides a design architecture that easily provides for substitutions and replacements of core function elements during the manufacturing process. According to some aspects of the disclosure, the modular IV assembly provides a single interface point to the user.

A modular IV assembly 100 is shown in FIGS. 2-10, according to some aspects of the disclosure. The modular IV assembly 100 includes a drip chamber 110, a flow control assembly 120, a filter assembly 130, an air vent assembly 140 (e.g., for a fluid path), an anti-run dry (ARD) member 150 and a check valve 160. Thus, the modular IV assembly provides one device that includes many different features, such as anti-run dry fluid flow, drop visibility, flow control, fluid filtering, air venting (e.g., line de-bubbling) and flow direction control from the check valve. The modular IV assembly 100 may have a large area below the drip chamber 110, thus providing an area for a user to grip easily.

The drip chamber 110 has a body 112 formed of a material suitable for use in infusion procedures. For example, the body 112 may be formed of a hard plastic that is not squeezable and thus also has an auto prime function. As another example, the body 112 may be formed of a flexible plastic that is squeezable and thus does not require an auto prime function. The body 112 may be transparent to provide drip visibility from the fluid entering the drip chamber 110. The drip chamber 110 is coupled to a base housing 170. For example, the body 112 may be an elongated cylinder having a base portion 113 that is coupled to a drip chamber coupling portion 172 of the base housing 170. The drip chamber coupling portion 172 includes an inlet port 173 that provides a fluid pathway from the drip chamber 110 into the base housing 170 (see FIGS. 6 and 7). Any size and shape is contemplated for the drip chamber 110 and correspondingly the drip chamber coupling portion 172. An inlet connector 114 is coupled to the body 112. The inlet connector 114 may be configured to receive an IV tube from a fluid source (e.g., IV bag), for example. As another example, the inlet connector 114 may be configured to connect directly to an IV fluid container (e.g., bag, bottle) via a spike connection.

The flow control assembly 120 is coupled to the base housing 170. The flow control assembly 120 includes a roller housing 122, a roller 124, and a flow control membrane 126. The roller housing 122 is sized and shaped to couple with the base housing 170. The roller 124 is movably coupled to the roller housing 122. For example, axles 125 of the roller 124 may be received within channels 123 disposed on opposing walls of the roller housing 122, where the axles 125 move axially along the channels 123 when the roller 124 is moved. The flow control membrane 126 is sized and shaped to be received within the base housing 170. The flow control membrane 126 may be formed of a flexible material (e.g., elastomer), such that flow control membrane 126 may flex into a fluid flow path 174 when the roller 124 engages the flow control membrane 126. In some aspects of the disclosure, the flow control assembly may include a different control member than the roller 124, such as a lever, a slider or a knob, for example.

Figure 12:
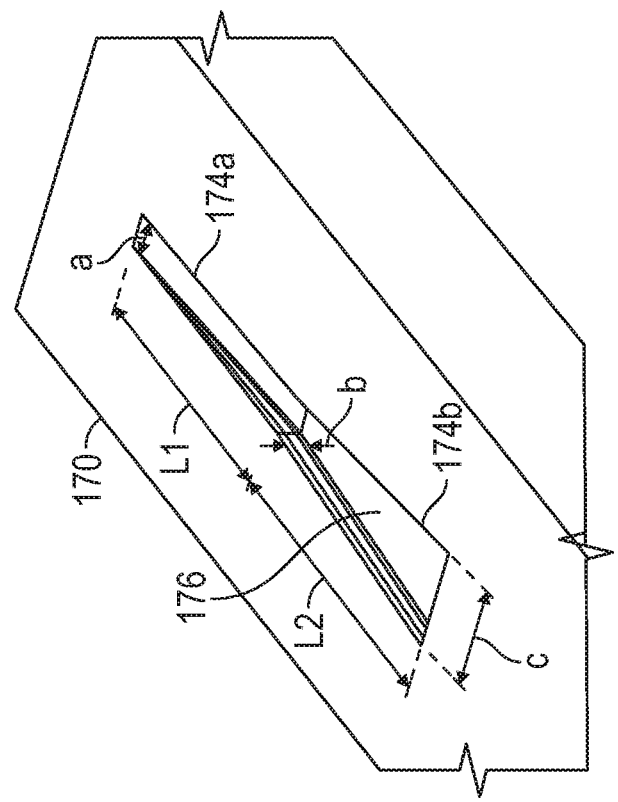
FIG. 12 is a partial perspective view of the base housing of FIG. 11, according to some aspects of the disclosure.
Figure 13:
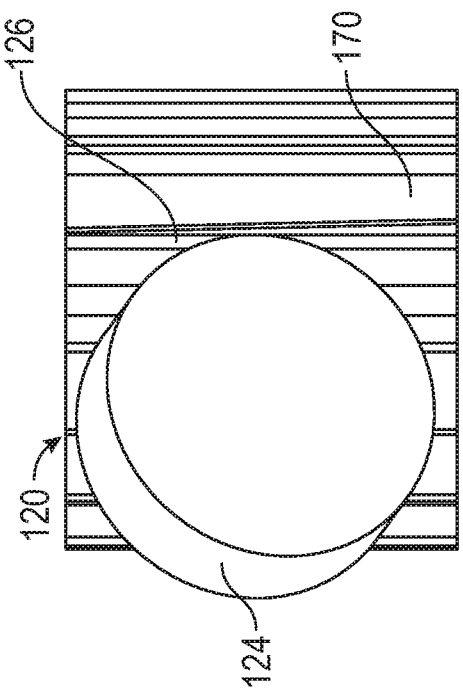
FIG. 13 is a partial perspective view of a flow control assembly of a modular IV assembly, according to some aspects of the disclosure.
Figure 11:
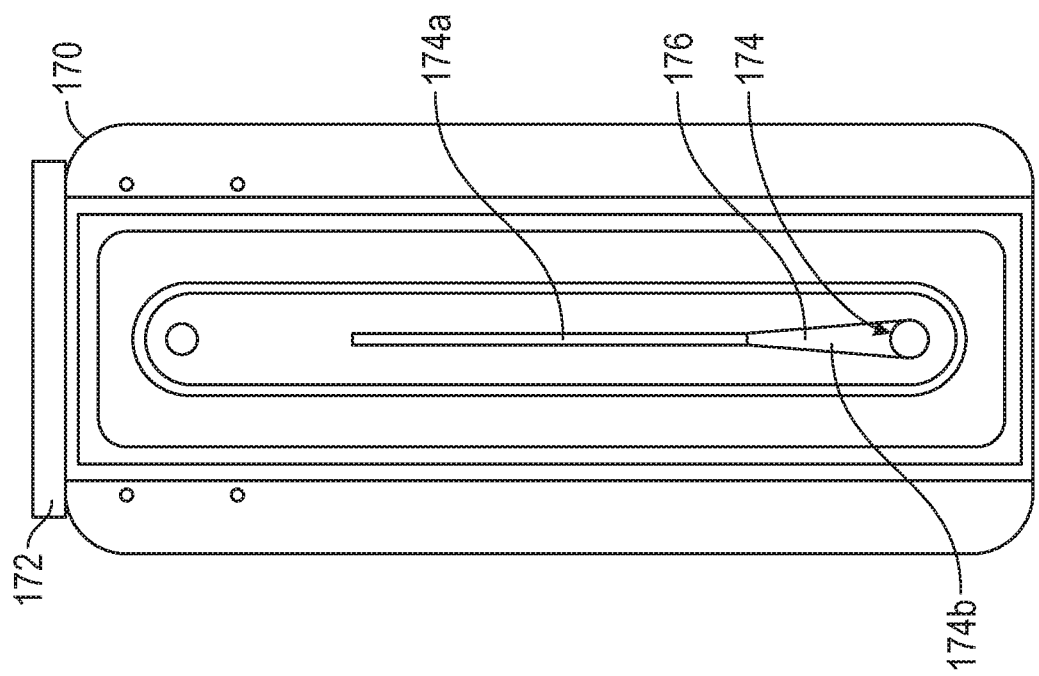
FIG. 11 is a front view of a base housing of a modular IV assembly, according to some aspects of the disclosure.

As shown in FIGS. 11-13, the base housing 170 may be formed of a hard plastic, where the fluid flow path 174 is formed by a cavity 176 disposed within a surface of the base housing 170. The cavity 176 may vary in both width and depth to provide different fluid flow rates based on the position of the roller 124. For example, the cavity 176 shown in FIG. 12 has a first section 174a having a length L1 of 15 mm and a width A of 0.75 mm, and a second section 174b having a length L2 of 15 mm and a width C of 2.5 mm. The depth of first section 174a increases from zero at one end to depth B of 0.5 mm at the other end. The depth of the second section 174b is a constant depth B of 0.5 mm. Any of the widths A and C, depth B and lengths L1 and L2 may be independently varied to tune the cavity 176, and therefore the fluid flow path 174, for a specific flow profile.

Figure 14:
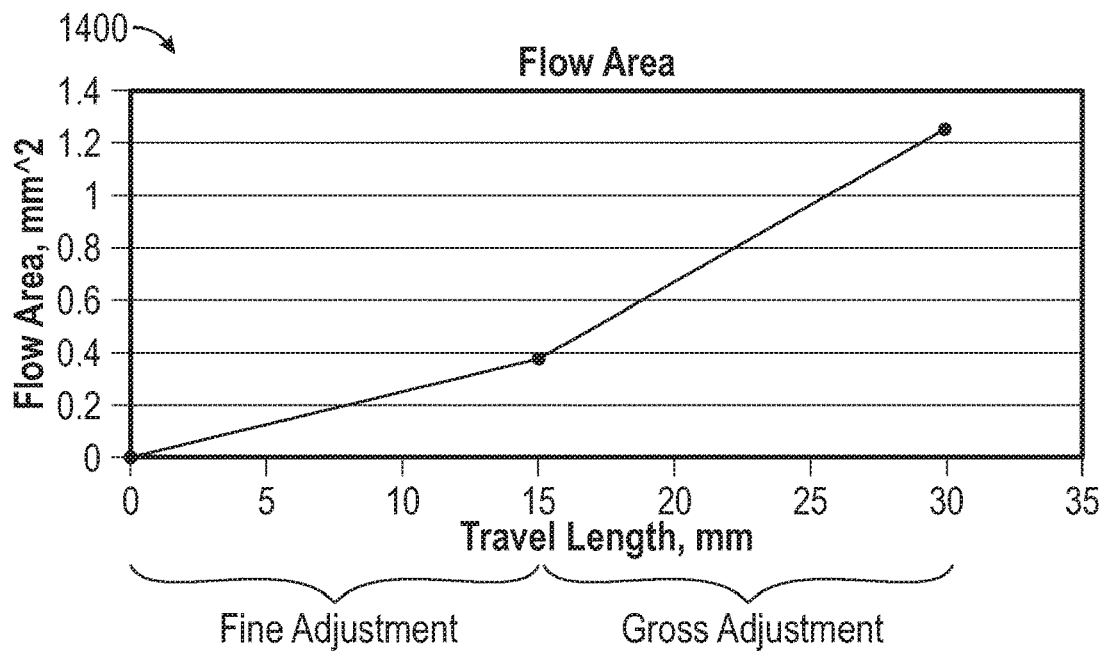
FIG. 14 is a graph depicting a variation in flow area based on the flow control assembly of FIG. 13.

As shown in FIG. 13, the portion of the roller 124 that engages the flow control membrane 126 causes the flow control membrane 126 to flex into the cavity 176, which blocks the fluid flow path 174 to varying degrees based on the position of the engaged portion of the roller 124 over the cavity 176. FIG. 14 shows a graph 1400 depicting the variation in flow area over the travel length of the roller 124 based on the above described values for A, B, C, L1 and L2. The flow area under the portion of the roller 124 that engages the flow control membrane 126 corresponds to a resulting fluid flow rate through the cavity 176, with the largest flow area providing a greater fluid flow rate and the smallest flow area providing a lesser fluid flow rate.

For example, when the roller 124 is positioned at the end of L1 with a depth of zero, the flow area is zero and the fluid flow path 174 is completely occluded (e.g., no fluid flow through the fluid flow path 174). When the roller 124 is positioned at the junction of the second end of L1 and the first end of L2, the fluid flow area is 0.375 mm$^2$ and the fluid flow path 174 is partially occluded, thus providing for a 30% fluid flow rate. When the roller 124 is positioned at the second end of L2, the fluid flow area is 1.25 mm$^2$ and the fluid flow path 174 is not occluded, thus providing for a 100% fluid flow rate (e.g., full open). As shown in FIG. 14, the first portion of the graph corresponding to the roller 124 engagement along length L1 indicates a fine adjustment portion of the flow control assembly 120, while the portion of the graph corresponding to the roller 124 engagement along the length L2 indicates a gross adjustment portion of the flow control assembly 120. According to some aspects of the disclosure, any number of flow variation areas may be provided, such as three or more, for example. Thus, there may be correspondingly more cavity sections than the first and second sections 174a, 174b, such as three or more cavity sections, for example.

Since the drip chamber 110 is coupled directly to the base housing 170, no IV tubing is necessary to link the drip chamber to the flow control assembly 120, as opposed to the infusion set 30 shown in FIG. 1 for which the drip chamber 40 and the roller clamp 60 are each coupled within the infusion set 30 via tubing 20. Further, since the flow control assembly 120 does not include or engage with flexible IV tubing, the fluid flow rate can be consistently provided and maintained through the life of the modular IV assembly 100. For example, the hard plastic of the base housing 170 does not deform (e.g., drift) over time. By contrast, a typical roller clamp 60 involves restricting fluid flow within soft, flexible tubing 20 by deforming the tubing 20, and the tubing 20 tends to relax (e.g., lose its resilience) over time, which makes it increasingly difficult to precisely control the fluid flow rate over time. Accordingly, the flow control assembly 120 is configured to provide consistent and precise control of the fluid flow rate through the modular IV assembly 100.

Figure 15:
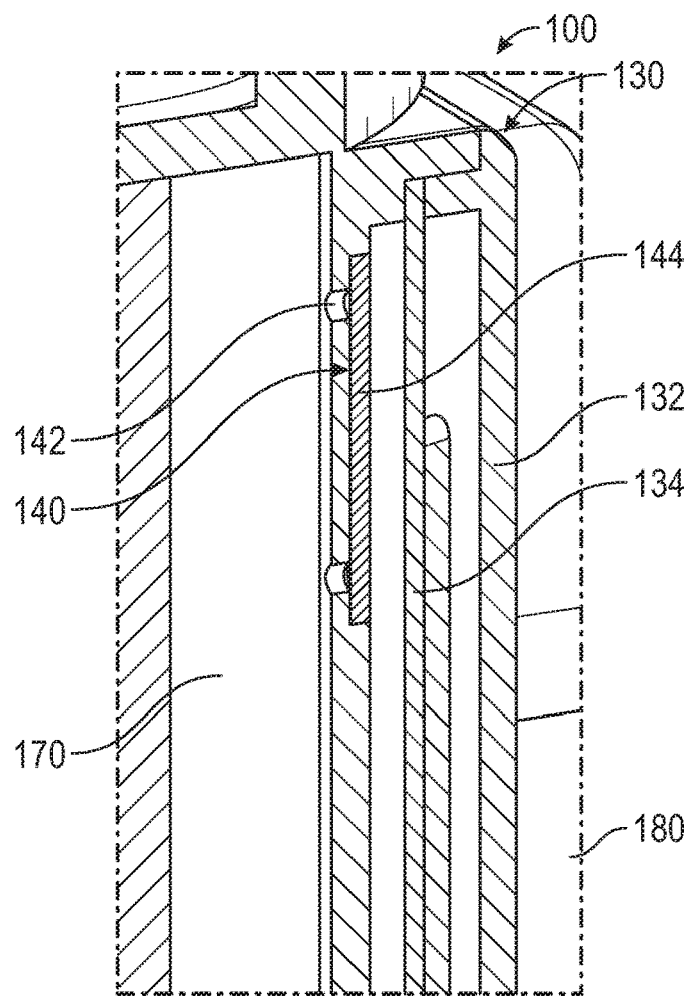
FIG. 15 is a partial perspective view of a modular IV assembly, according to some aspects of the disclosure.
Figure 16:
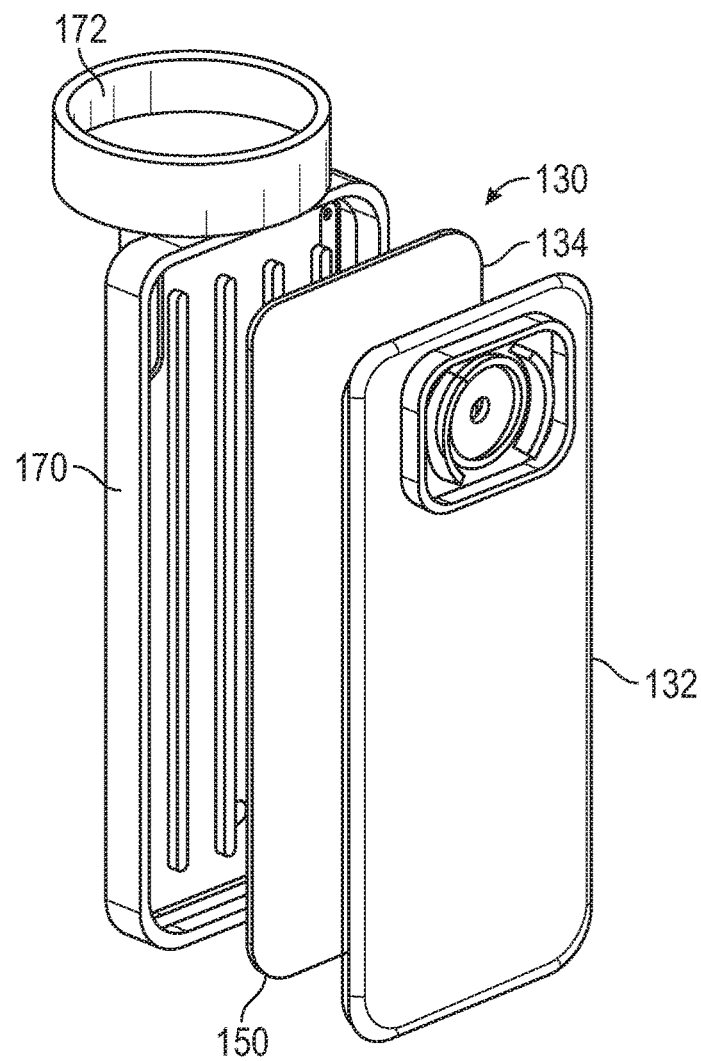
FIG. 16 is an exploded perspective view of the modular IV assembly of FIG. 15, according to some aspects of the disclosure.
Figure 17:
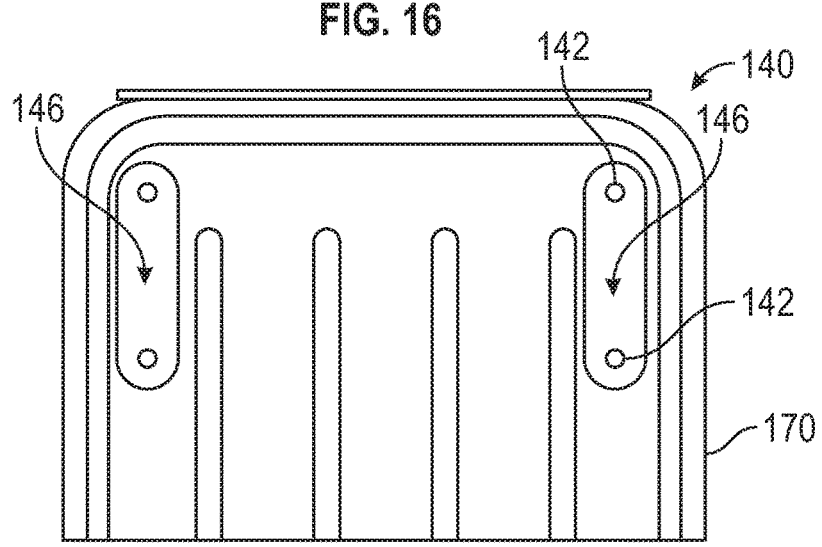
FIG. 17 is a front view of a portion of an air vent assembly of a modular IV assembly, according to some aspects of the disclosure.
Figure 19:
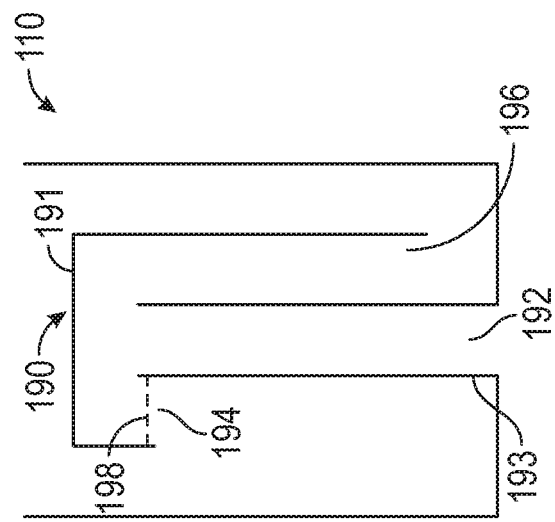
FIG. 19 is a front view of a self-leveling assembly of the drip chamber of FIG. 18, according to some aspects of the disclosure.
Figure 18:
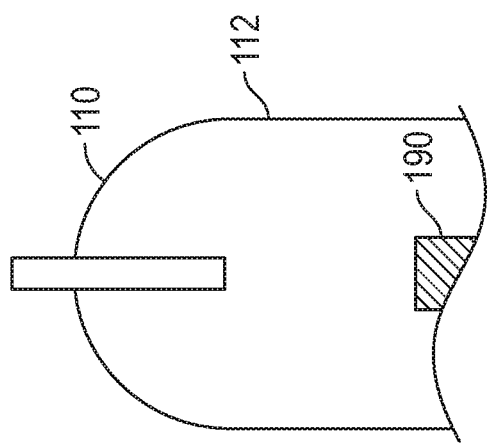
FIG. 18 is a front view of a drip chamber of a modular IV assembly, according to some aspects of the disclosure.

As shown in FIGS. 15-17, the base housing 170 is also configured to couple with a filter assembly 130 on an opposing side of the base housing 170 from the flow control assembly 120. The filter assembly 130 includes a filter housing 132 that engages and traps a filter membrane 134 against the base housing 170. The filter membrane 134 is formed from a hydrophilic material that prevents air from passing through the filter membrane 134 once the filter membrane 134 is wetted. Thus, only liquid may pass through the filter membrane 134 from the base housing 170. The filter membrane 134 material may be designed or chosen for specific filtering properties in order to filter out particular elements from the fluid passing through the filter assembly 130. For example, the filter membrane 134 may be formed to filter out particles larger than a particular size (e.g., 15 um, 5 um, 1.2 um, 0.2 um).

The base housing 170 also includes a portion on the same side as the filter assembly 130 on which the air vent assembly 140 is disposed. The air vent assembly 140 includes vent ports 142 in a vent cavity 146 in the base housing 170 and an air vent membrane 144 disposed in the vent cavity 146 over the vent ports 142. The air vent membrane 144 is formed from a small pore hydrophobic material that prevents liquid from passing through the air vent membrane 144 while allowing gas (e.g., air) to vent out of the fluid flow path 174 through the vent ports 142 (e.g., back into the drip chamber 110).

Figure 5:
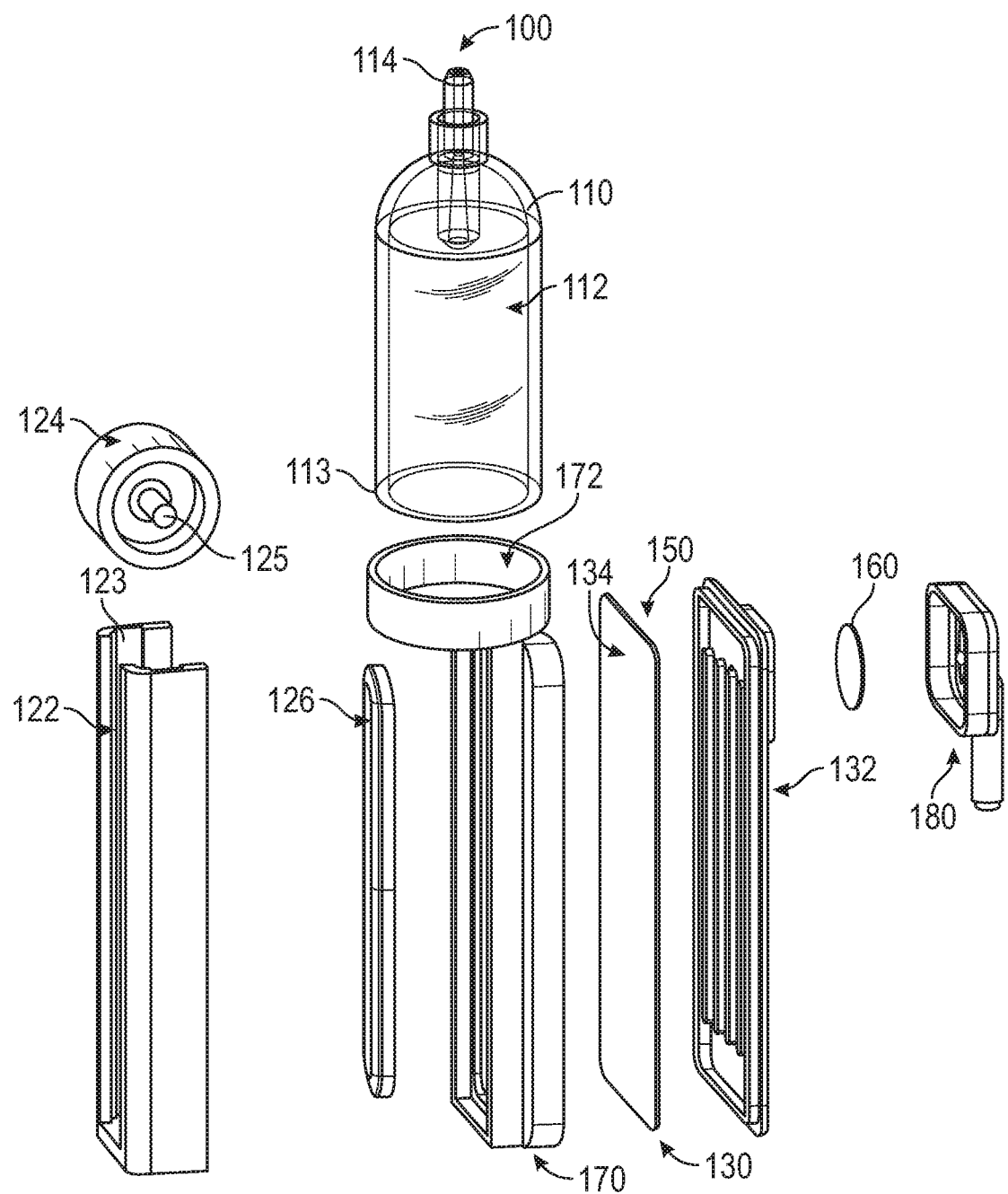
FIG. 5 is an exploded perspective view of the modular IV assembly of FIG. 2, according to some aspects of the disclosure

The ARD member 150 is shown in FIG. 5 as being integral with the filter membrane 134. For example, the filter membrane 134 material may be designed or chosen to provide ARD features as well as filtering features. In some aspects of the disclosure, the ARD member 150 may be an ARD material and the filter membrane 134 may be a different filtering material combined together (e.g., separate layers, integrally formed) into one membrane with both filtering and ARD properties.

As shown in FIG. 5, the check valve 160 is disposed between an exit cavity 162 on the outer surface of the filter housing 132 and a fluid exit housing 180. The check valve 160 may be formed from a flexible material and act as a one-way valve that allows fluid to flow from a fluid port 164 in the exit cavity 162 out through an exit port 182 in the fluid exit housing 180, while preventing fluid flow in the opposing direction from the exit port 182 to the fluid port 164. The fluid exit housing 180 also includes an outlet port 184 configured to be coupled to IV tubing, such as IV tubing connected to an infusion pump or a catheter, for example. The check valve 160 and fluid exit housing 180 may be disposed at the top end of the base housing 170 as shown in FIG. 5, or at the bottom or base portion of the base housing 170 as shown in FIGS. 8 and 9.

In operation, as shown in FIG. 7, the modular IV assembly 100 provides a fluid flow path 174 that begins upon entry of fluid from the drip chamber 110 and ends upon exit of fluid from the exit port 182. The fluid flow path 174 includes flow of fluid through the flow control assembly 120 at a flow rate set by the position of the roller 124 in relation to the cavity 176. The fluid exits the cavity 176 and flows into contact with the filter membrane 134 and ARD member 150. The fluid is filtered through the filter membrane 134 and exits into the filter housing 132 and out through the fluid port 164. The fluid then flows past and/or through the check valve 160 and out through the exit port 182 to the outlet port 184. Since air trapped in the fluid cannot pass through the filter membrane 134, the air instead passes through the air vent membrane 144 into the vent ports 142 and out of the base housing 170 portion of the modular IV assembly 100.

Figure 10:
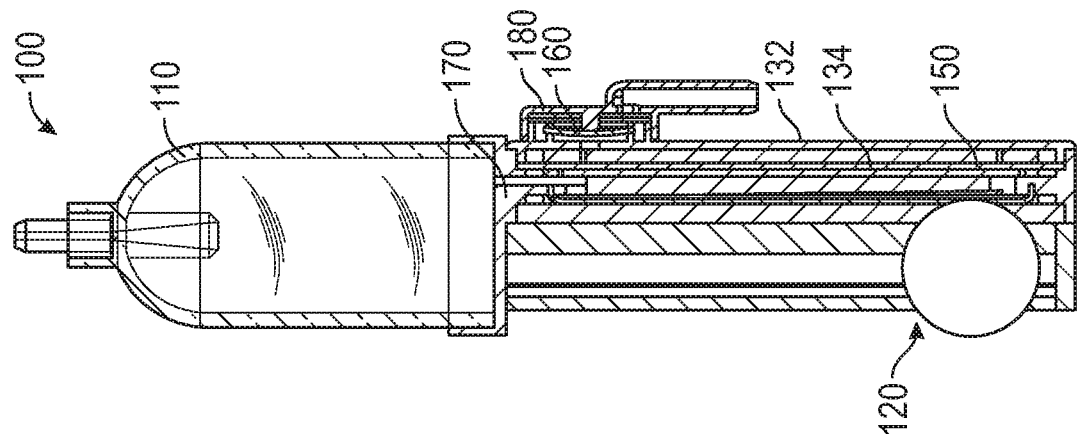
FIG. 10 is a cross-sectional side view of a modular IV assembly, according to some aspects of the disclosure.
Figure 9:
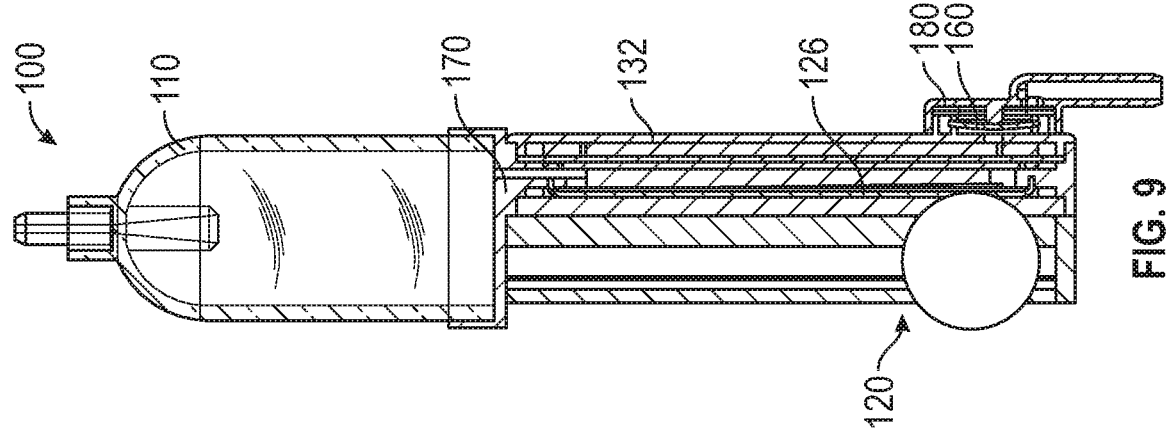
FIG. 9 is a cross-sectional side view of a modular IV assembly, according to some aspects of the disclosure.
Figure 8:
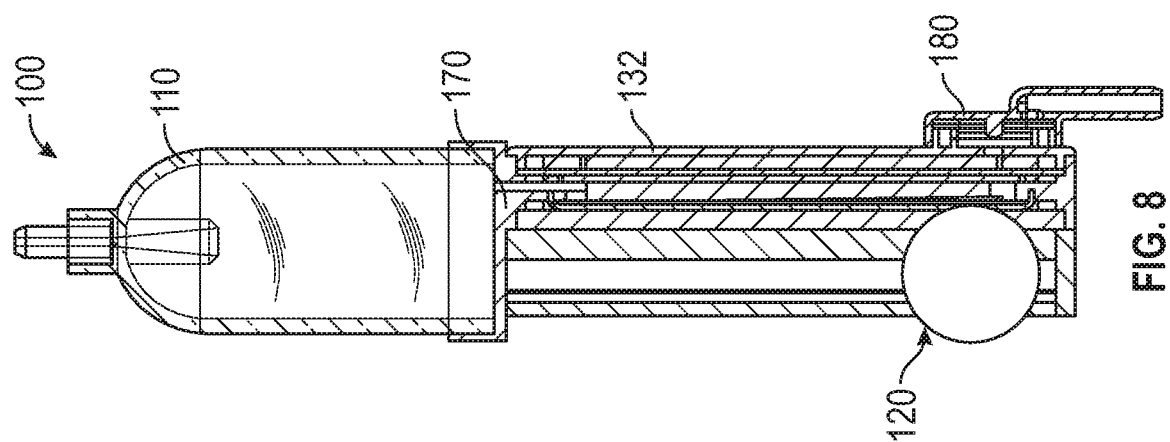
FIG. 8 is a cross-sectional side view of a modular IV assembly, according to some aspects of the disclosure.

As shown in FIGS. 8-10, the modular IV assembly 100 may be configured to include any or all of the above described components while maintaining the same or similar outward package and appearance. For example, FIG. 8 depicts a base modular IV assembly 100 including the drip chamber 110 and the flow control assembly 120 only, with no filter assembly 130, air vent assembly 140, ARD member 150 or check valve 160. Here, fluid flows into the base housing 170 from the drip chamber 110 and flows out the outlet port 184 at a flow rate set by the flow control assembly 120. FIG. 9 depicts a more integrated modular IV assembly 100 by adding the check valve 160 to the base modular IV assembly 100 shown in FIG. 8. Similarly, FIG. 10 depicts an even more integrated modular IV assembly 100 by adding a filter membrane 134 and an ARD member 150 to the modular IV assembly 100 shown in FIG. 9. The air vent membrane 144 may further be added to any of the above-described modular IV assemblies 100. Accordingly, the exterior of any modular IV assembly 100 may be defined by the drip chamber 110, the roller housing 122, the base housing 170, the filter housing 132 and the fluid exit housing 180. Here, the external form of modular IV assembly 100 package may remain constant regardless of the presence of absence of the internal components (e.g., filter assembly 130, air vent assembly 140, ARD member 150, check valve 160).

As shown in FIGS. 18-22, the drip chamber 110 may include a self-leveling assembly 190, according to aspects of the disclosure. The body 112 of the drip chamber 110 may act as both an air trap and a drop visibility chamber. The self-leveling assembly 190 has a top housing portion 191 and a bottom housing portion 193, where the bottom housing portion 193 may be disposed at the base portion 113 of the body 112. The self-leveling assembly 190 includes a leveling outlet port 192 that is aligned with the inlet port 173 in the drip chamber coupling portion 172 of the base housing 170. The self-leveling assembly 190 also includes leveling fluid inlets 194, 196 disposed adjacent to the leveling outlet port 192. Here, the leveling fluid inlet 194 has a shortened flow path and is disposed near the top housing portion 191 (e.g., away from the base portion 113), while the leveling fluid inlet 196 has a lengthened flow path and is disposed near the bottom housing portion 193 (e.g., close to the base portion 113). A barrier 198 (e.g., hydrophilic membrane, air check valve) is disposed within the leveling fluid inlet 194.

As shown in FIG. 20, when the liquid level in the drip chamber 110 covers leveling fluid inlet 196 and does not cover leveling fluid inlet 194, air trapped in the body 112 is vented out through the leveling outlet port 192. As shown in FIG. 21, when the liquid level in the drip chamber 110 rises to cover both leveling fluid inlet 196 and leveling fluid inlet 194, the barrier 198 prevents air from passing through and subsequently only liquid (e.g., saline solution) passes out through the leveling outlet port 192. Here, liquid can freely enter/pass through leveling fluid inlet 196 and may also enter/pass through leveling fluid inlet 194 at a slower rate due to the barrier 198. As shown in FIG. 22, when enough liquid siphons out through the leveling outlet port 192 that the leveling fluid inlet 194 is again exposed to air in the body 112, the liquid continues to enter/pass through the leveling fluid inlet 196 only while the air is blocked from passing through the barrier 198.

For example, the barrier 198 may be a membrane formed from a hydrophilic material that prevents air from passing through the barrier 198 once the barrier 198 is wetted. Thus, in FIG. 20 the barrier 198 is not yet wetted, so air may pass through and exit the leveling outlet port 192. Once the barrier 198 is wetted in FIG. 21, the barrier 198 prevents air from passing through. When the liquid recedes from the barrier 198 in FIG. 22, the barrier 198 is still wetted and thus continues to prevent air from passing through until it dries out.

As another example, the barrier 198 may be an air check valve that allows air to pass through the barrier 198 while preventing liquid from passing through the barrier 198. Thus, in FIG. 20 the barrier 198 is open to the air in the body 112, so air may pass through and exit the leveling outlet port 192. Once the barrier 198 is submerged under the liquid level in FIG. 21, the barrier 198 prevents liquid from passing through leveling fluid inlet 194 and thus the liquid only enters/passes through leveling fluid inlet 196 and out the leveling outlet port 192. When the liquid recedes from the barrier 198 in FIG. 22, the pressure exerted by the liquid trapped above the barrier 198 within the self-leveling assembly 190 may prevent air from passing through the barrier 198 while liquid continues to enter/pass through the leveling fluid inlet 196 and out the leveling outlet port 192.

The self-leveling assembly 190 eliminates the need to prime the drip chamber 110 by squeezing a flexible body 112 to push air out and to allow fluid to enter through the inlet connector 114. Thus, the self-leveling assembly 190 provides for venting air from the drip chamber 110 regardless of whether the body 112 is flexible (e.g., flexible plastic) or stiff (e.g., hard plastic). Further, the self-leveling assembly 190 may prevent microbubbles from entering the fluid.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

The invention claimed is:

1. A modular intravenous (IV) assembly, comprising:
   a drip chamber having a body and an inlet connector;
   a base housing coupled directly to a base portion of the drip chamber, the base housing having an inlet port in fluid connection with the drip chamber and a flow path cavity in fluid connection with the inlet port, wherein the flow path cavity comprises a first flow area having a constant width and a varying depth, and a second flow area having a varying width and a constant depth; and
   a flow control assembly coupled directly to a first portion of the base housing, the flow control assembly comprising:
      a roller housing;
      a roller; and
      a flow control membrane disposed between the roller and the flow path cavity in the base housing.

2. The modular IV assembly of claim 1, wherein the flow control assembly is configured to prevent fluid flow through the base housing when the roller is engaged with the flow control membrane adjacent to a start position of the first flow area.

3. The modular IV assembly of claim 1, wherein the flow control assembly is configured to provide full fluid flow through the base housing when the roller is engaged with the flow control membrane adjacent to an end portion of the second flow area.

4. The modular IV assembly of claim 1, wherein the flow control assembly is configured to provide increasing fluid flow through the base housing as the roller engaged with the flow control membrane moves from an end portion of the second flow area.

5. The modular IV assembly of claim 1, further comprising a filter assembly coupled directly to a second portion of the base housing.

6. The modular IV assembly of claim 5, wherein the first and second portions are on opposing surfaces of the base housing.

7. The modular IV assembly of claim 5, wherein the filter assembly comprises:
   a filter housing coupled directly to the second portion of the base housing; and
   a filter membrane disposed between the filter housing and the second portion of the base housing.

8. The modular IV assembly of claim 7, wherein the filter membrane comprises a hydrophilic material that prevents gas from passing through the filter membrane when the filter membrane is wetted.

9. The modular IV assembly of claim 7, wherein a first surface of the filter membrane is disposed adjacently at a distance from an inner surface of the second portion of the base housing, and wherein a space between the inner surface of the second portion and the first surface of the filter membrane is configured to provide a flow path for fluid entering the second portion of the base housing from the flow control assembly.

10. The modular IV assembly of claim 9, wherein a second surface of the filter membrane is disposed adjacently at a distance from an inner surface of the filter housing, and wherein a space between the inner surface of the filter housing and the second surface of the filter membrane is configured to provide a flow path for fluid passing through the filter membrane.

11. The modular IV assembly of claim 7, further comprising an anti-run dry member comprising one of an individual layer disposed on the filter membrane and an integrally formed material comprising the filter membrane.

12. The modular IV assembly of claim 1, further comprising:
   a filter housing coupled directly to a second portion of the base housing;
   a fluid exit housing coupled directly to the filter housing; and
   a one-way check valve disposed between an exit cavity in an outer surface of the filter housing and the fluid exit housing, the check valve configured to allow fluid to flow out from the exit cavity through an exit port in the fluid exit housing while preventing fluid from flowing in an opposing direction into the exit cavity.

13. The modular IV assembly of claim 12, wherein the fluid exit housing, the check valve and the exit cavity are disposed at a top portion of the base housing adjacent to the drip chamber.

14. The modular IV assembly of claim 12, wherein the fluid exit housing, the check valve and the exit cavity are disposed at a bottom portion of the base housing.

15. The modular IV assembly of claim 1, further comprising an air vent assembly coupled directly to a second portion of the base housing, wherein the first and second portions are on opposing surfaces of the base housing, the air vent assembly comprising:
   a vent cavity disposed in the second portion of the base housing;
   a vent port disposed in the vent cavity, the vent port coupled to an air flow path in the base housing; and
   an air vent membrane disposed in the vent cavity.

16. The modular IV assembly of claim 15, wherein the air vent membrane comprises a small pore hydrophobic material that prevents liquid from passing through the air vent membrane into the vent port while allowing gas to pass through the air vent membrane and vent out through the vent port.

17. The modular IV assembly of claim 1, wherein the drip chamber further comprises a self-leveling assembly, the self-leveling assembly comprising:
   a bottom housing portion disposed at the base portion of the drip chamber and adjacent to the base housing;
   a leveling outlet port aligned with the inlet port in the base housing;
   first and second leveling inlet ports disposed adjacent opposing sides of the leveling outlet port; and
   a barrier disposed within the first leveling inlet port.

18. An intravenous (IV) set, comprising:
   a modular IV assembly, the modular IV assembly comprising:
      a drip chamber having a body and an inlet connector;
      a base housing coupled directly to a base portion of the drip chamber, the base housing having an inlet port in fluid connection with the drip chamber and a flow path cavity in fluid connection with the inlet port;
      a flow control assembly coupled directly to a first portion of the base housing, the flow control assembly comprising;

a roller housing;
a roller; and
a flow control membrane disposed between the roller and the flow path cavity in the base housing;
a filter housing coupled directly to a second portion of the base housing;
a fluid exit housing coupled directly to the filter housing; and
a one-way check valve disposed between an exit cavity in an outer surface of the filter housing and the fluid exit housing, the check valve configured to allow fluid to flow out from the exit cavity through an exit port in the fluid exit housing while preventing fluid from flowing in an opposing direction into the exit cavity;
a fluid container coupled to the inlet connector of the drip chamber by a first IV tube; and
a fluid delivery member coupled to the modular IV assembly by a second IV tube.

19. A method of delivering a medical fluid, the method comprising:
coupling a fluid container to a modular intravenous (IV) assembly with a first IV tube, the modular IV assembly including a drip chamber having a body and an inlet connector, a base housing coupled directly to a base portion of the drip chamber, the base housing having an inlet port in fluid connection with the drip chamber and a flow path cavity in fluid connection with the inlet port and a flow control assembly coupled directly to a first portion of the base housing, the flow control assembly including a roller housing, a roller and a flow control membrane disposed between the roller and the flow path cavity in the base housing, wherein the flow path cavity comprises a first flow area having a constant width and a varying depth, and a second flow area having a varying width and a constant depth;
coupling a fluid delivery member to the modular IV assembly with a second IV tube; and
adjusting a fluid flow rate from the modular IV assembly to the fluid delivery member by moving the roller in the flow control assembly.

20. An IV set, comprising:
the modular IV assembly of claim 1;
a fluid container coupled to the inlet connector of the drip chamber by a first IV tube; and
a fluid delivery member coupled to the modular IV assembly by a second IV tube.

* * * * *